(12) United States Patent
Reinhardt et al.

(10) Patent No.: US 7,278,522 B2
(45) Date of Patent: Oct. 9, 2007

(54) CONTROLLABLE MOTION DAMPER

(75) Inventors: Holger Reinhardt, Kempen (DE); Hans Schönemann, Neustadt (DE)

(73) Assignee: Bauerfeind AG, Zeulenroda (DE)

( * ) Notice: Subject to any disclaimer, the term of this patent is extended or adjusted under 35 U.S.C. 154(b) by 130 days.

(21) Appl. No.: 11/128,164

(22) Filed: May 13, 2005

(65) Prior Publication Data

US 2005/0258009 A1  Nov. 24, 2005

(30) Foreign Application Priority Data

May 19, 2004 (DE) .................. 20 2004 008 024 U (51) Int. Cl.
*F16F 9/53* (2006.01)
(52) U.S. Cl. .............................. 188/267.2; 188/266.3; 188/269; 188/294
(58) Field of Classification Search ................ 188/267, 188/267.1, 267.2, 266.3, 266.4, 269, 290, 188/294, 296
See application file for complete search history.

(56) References Cited

U.S. PATENT DOCUMENTS

| | | | |
|---|---|---|---|
| 160,486 A | | 3/1875 | Towns |
| 3,059,915 A * | 10/1962 | Kemelhor .................... 267/126 |
| 4,896,754 A * | 1/1990 | Carlson et al. ............. 192/21.5 |
| 5,161,653 A | 11/1992 | Hare, Sr. |
| 5,353,897 A | 10/1994 | Woessner |
| 5,452,745 A | 9/1995 | Kordonsky et al. |
| 5,538,117 A * | 7/1996 | Bouchez ...................... 188/371 |
| 5,956,951 A | 9/1999 | O'Callaghan |
| 6,113,642 A | 9/2000 | Petrofsky et al. |
| 6,302,249 B1 * | 10/2001 | Jolly et al. .................. 188/269 |
| 6,318,522 B1 * | 11/2001 | Johnston et al. .......... 188/267.2 |
| 6,419,057 B1 * | 7/2002 | Oliver et al. ............. 188/267.2 |
| 6,423,098 B1 | 7/2002 | Biedermann |
| 6,439,356 B1 * | 8/2002 | Butera et al. ............. 188/267.2 |
| 6,740,125 B2 | 5/2004 | Mosler |
| 6,752,425 B2 * | 6/2004 | Loh et al. .................... 280/779 |
| 6,955,249 B2 * | 10/2005 | Biasiotto et al. .......... 188/267.1 |
| 7,066,308 B2 * | 6/2006 | Kanno et al. ............... 188/290 |
| 2002/0014380 A1 * | 2/2002 | Jolly et al. .................. 188/269 |
| 2004/0195062 A1 * | 10/2004 | Anderfaas et al. ........ 188/267.2 |
| 2005/0121269 A1 * | 6/2005 | Namuduri ................. 188/267.1 |

FOREIGN PATENT DOCUMENTS

DE  44 97 719 T1  10/1993

(Continued)

*Primary Examiner*—Devon Kramer
(74) *Attorney, Agent, or Firm*—Birch, Stewart, Kolasch & Birch, LLP (57) ABSTRACT

A controllable motion damper with a damping piston separating two damping chambers from each other in a damping cylinder. A damping valve is disposed in a connecting channel of the two damping chambers with the transmissivity of the damping valve for a damping fluid contained in the motion damper being controlled by a control device. Both damping chambers are filled with an electromagnetically uninfluenceable damping fluid. The control device includes a slide piston unit filled with a magnetorheological fluid. The slide piston unit includes a slide piston operatively coupled to the damping piston, wherein, through the intermediary of the magnetorheological fluid, the magnetorheological fluid is influenceable by controllable magnetic field generators with regard to its flow resistance with the slide piston acting on an actuator connected to the damping valve for controlling the movement of the damping piston.

10 Claims, 6 Drawing Sheets

FOREIGN PATENT DOCUMENTS

| | | |
|---|---|---|
| DE | 102 14 357 A1 | 10/2003 |
| DE | 102 40 568 A1 | 11/2004 |
| EP | 0 957 838 B1 | 11/1999 |
| GB | 2 267 947 A | 12/1993 |
| GB | 23 28 160 | 2/2003 |
| WO | WO93/25827 | 12/1993 |
| WO | 11-190379 | 7/1999 |
| WO | WO99/27273 | 10/2000 |

* cited by examiner

CONTROLLABLE MOTION DAMPER

BACKGROUND OF THE INVENTION

1. Field of the Invention

The invention relates to a controllable motion damper with a damping piston, said damping piston separating two damping chambers from each other in a damping cylinder, and with a damping valve disposed in a connecting channel of the two damping chambers, the transmissivity of said damping valve for a damping fluid contained in the motion damper being controlled by a control device.

2. Description of Background Art

Such a controllable motion damper for an artificial knee joint is known from DE-OS 10214357. The damping cylinder in said motion damper is filled with a magnetorheological fluid serving as damping fluid, said magnetorheological fluid being displaced by the axial movement of a damping piston in the damping cylinder, wherein the magnetorheological fluid flows through a damping valve, said damping valve connecting the two cylinder chambers in the damping cylinder, said cylinder chambers being separated by the damping piston. Depending on the transmissivity of the damping valve, correspondingly larger or smaller forces acting on the damping piston are required in order to displace the damping piston and thus to achieve the desired damping effect. In the known motion damper, the device controlling the transmissivity of the damping valve is in the form of one or more electromagnets which, through a magnetic field controlled for higher or lower intensity, correspondingly change in known manner the viscosity of the magnetorheological fluid and thus its flow resistance in the damping cylinder. In the known publication, two illustrative embodiments are provided for the arrangement of the damping valve. According to one embodiment, the damping valve consists of a gap between the damping valve and the damping piston, the gap being permeated by a controllable magnetic field. According to a further embodiment, the two damping chambers separated by the damping piston are connected by a bypass channel in which the magnetorheological fluid flows when the damping piston moves. The bypass channel passes through a magnetic field generator, wherein the controllable magnetic field of said magnetic field generator controls the viscosity of the magnetorheological fluid flowing in the region of the magnetic field in the respectively desired manner for more or less damping.

A further known motion damper is described in EP 0957838 B1, said motion damper likewise containing a magnetorheological fluid as the damping fluid.

The magnetorheological fluid (MRF) used in the known motion dampers is a fluid which, because it contains small magnetizable particles, has a high relative density in the range of approximately 3, this therefore being close to half the relative density of iron. Consequently, in view of the required fluid charges of the motion damper, the motion damper is made very heavy, this representing a considerable disadvantage with regard to its practical use. Above all, the viscosity of an MRF cannot be increased at will, i.e. saturation occurs, which means that, in spite of higher magnetic power, it is not possible to achieve any increase in damping.

Further known from the international application WO 99/27273 is a motion damper in which, for the purpose of reducing the volume of a magnetorheological fluid in the damper, one damping chamber thereof contains a conventional damping fluid, e.g. oil, while the other damping chamber contains the magnetorheological fluid, which, however, additionally acts as the damping fluid, thereby accounting for a considerable proportion of the weight of the motion damper.

Also known are motion dampers for artificial knee joints in which only a conventional damping fluid, especially oil, is used (e.g. U.S. Pat. No. 6,113,642) and in which the control of the throughflow of the damping fluid is accomplished by means of electromagnetically operated slide valves in the form of damping valves, the operation of which requires considerable electrical currents, this necessitating a correspondingly strong power supply for the damper.

Such motion dampers for artificial legs are controlled by programs which are stored in electronic controllers. An example thereof is contained in GB 2328160 A.

SUMMARY AND OBJECTS OF THE INVENTION

The object of the invention is to design the actual motion damper with damping cylinder, damping piston and damping valve such that said motion damper has a high power-to-weight ratio, low power consumption and a fast response.

The object of the invention is achieved in connection with the initially indicated motion damper in that both damping chambers are filled with an electromagnetically uninfluenceable damping fluid, the control device having a slide piston unit filled with a magnetorheological fluid, said slide piston unit having a slide piston non-positively coupled to the damping piston, wherein, through the intermediary of the magnetorheological fluid, said magnetorheological fluid being influenceable by a controllable magnet with regard to its flow resistance, said slide piston acts on an actuator connected to the damping valve.

In said thus designed motion damper, the immediate damping region contains no magnetorheological fluid whatsoever, with the result that, in comparison with the known similar motion dampers, the relevant region of the motion damper has considerably less weight, since it contains only a normal damping fluid, i.e. damping oil or gas, especially air. In comparison with the space required by the actual motion damper, the magnetorheological fluid contained in the control device is confined to a relatively small space serving merely to fill the control device, wherein, however, this does not involve any appreciable damping effect, but merely the transmission of small forces which provide for easy control of the damping valve, said damping valve being responsible for the degree of damping of the motion damper.

Furthermore, since the motion damper is kept free from the use of a magnetorheological fluid, there is the essential advantage of a sharp reduction in the wear phenomena otherwise caused by said fluid, said wear phenomena being attributable to the magnetizable particles added to the fluid and having, of course, a particularly pronounced impact when considerable forces need to be cushioned in the motion damper, as is the case, for example, with an artificial knee joint. Such wear has an impact above all in the region of required sealing elements, which, if conventional damping oil is used, exhibit no wear whatsoever in this regard, because they are lubricated by the damping oil.

In the motion damper according to the invention, the magnetorheological fluid is concentrated on the slide piston unit, which, however, is of small physical size, i.e. which is not of excessive weight. Furthermore, the slide piston unit transmits only relatively small forces, namely those forces which act on the damping valve, it being the case, however, that said damping valve requires no particular expenditure of force whatsoever for the purpose of adjustment, this having an especially wear-reducing effect. The therefor required forces are, as it were, diverted from the damping piston, since the damping piston is non-positively coupled to the slide piston of the slide piston unit, with the result, therefore, that no additional force generator is required for operating the slide piston unit or the damping valve it controls.

An advantageous mode of control of the slide piston unit can be accomplished in that the slide piston unit contains two actuating chambers separated by the slide piston, with a bypass channel interconnecting said actuating chambers, the flow resistance of said bypass channel being adjustable by the magnetic field generators. The bypass channel makes it possible in advantageous manner to control the action of the slide piston unit on the actuator by means of the magnetic field generator acting on the bypass channel.

In an advantageous embodiment, the damping valve is connected to a ram forming the actuator and guided by a restoring spring, said ram being adjustably connected to a partition wall, said partition wall dividing the slide piston unit into the two actuating chambers interconnected by the bypass channel. The consequence of this is that, after each phase of movement, the actuator and therefore the damping valve are returned to their normal positions, out of which positions said two components of the motion damper are then moved depending on the nature, particularly on the speed, of a newly commencing phase of movement, in order to achieve the desired effect on said phase.

A clear arrangement of the slide piston unit in relation to the damping cylinder is accomplished if the damping valve is disposed next to the damping cylinder and the slide piston unit is coaxial with the damping cylinder. Alternatively, however, it is also possible for the damping valve to be coaxial with the damping piston and for it to be a constituent part of the damping piston, this resulting in an especially compact design.

With regard to the design of the motion damper, it is possible, on the one hand, for a damping piston to be coaxially disposed and moved in a damping cylinder, as is the case, for example, in automobile shock absorbers. Alternatively, however, it is also possible for the motion damper and the slide piston unit each to be in the form of a rotary piston and for the damping valve and the bypass channel each to be provided in a sectorially extending wall, the damping valve being in the form of a rotary valve and the bypass channel containing a rotary vane as a constituent part of the actuator, wherein rotary valve and rotary vane are interconnected by a rotary shaft and are held in their normal positions by a torsion spring. This, therefore, is essentially a rotationally symmetrical arrangement which likewise provides advantageous possibilities of attachment.

A particular possibility of controlling the damping valve consists in that the damping valve is connected to the actuator by a control piston, said actuator containing in its slide piston unit a plurality of bypass channels each adjustable by a magnetic field generator, wherein, depending on the activation of the individual magnetic field generators, said bypass channels adjust the control piston to any desired positions and more especially to positions which follow the movement of the slide piston. With such a slide piston unit, which can be selectively controlled independently of a restoring device, it is possible through corresponding adjustment of the magnetic field generators to achieve any desired control of the damping valve, including latent damping settings with the slide piston moving and the magnetic field generator inactive, wherein such a form of control may originate, for example via sensors, from a program on a minicomputer, said program being designed for certain motion sequences of the motion which is to be damped, e.g. medically required forms of motion damping.

Instead of the magnetorheological fluid for operating the control device, it is also possible to use a fluid which is of equivalent effect, namely an electrorheological fluid, the viscosity of which is influenced by an electric field.

It should also be pointed out that the controllable motion damper according to the invention is suitable for use not only in prostheses, more particularly in artificial legs, but also in other applications involving the damping of a reciprocating motion, as is the case in a shock absorber.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIGS. 5a-e show the design of a motion damper in which the motion damper and the slide piston unit are each in the form of a rotary piston cylinder;

DETAILED DESCRIPTION OF THE PREFERRED EMBODIMENTS

Figure 1:
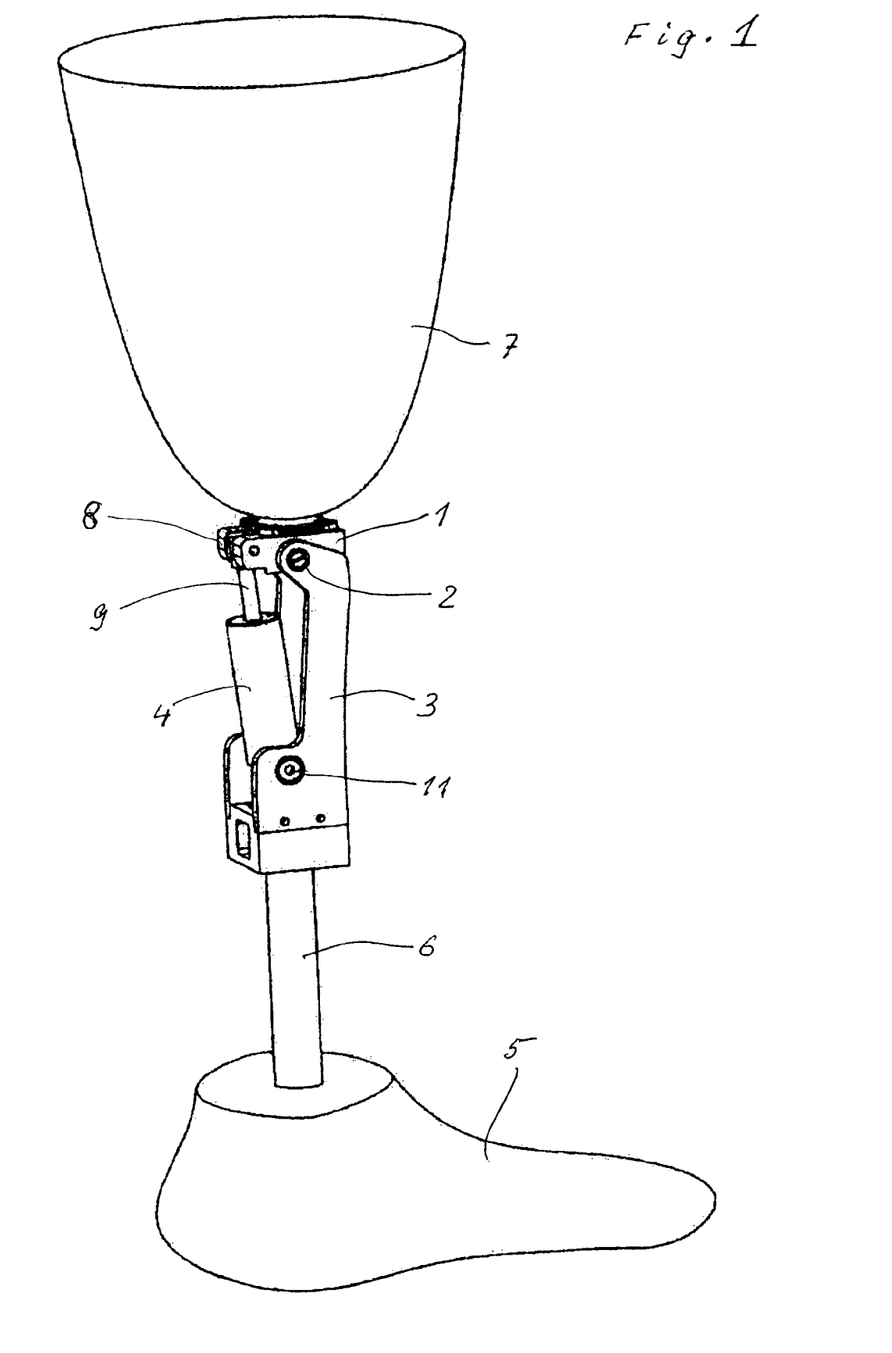
FIG. 1 shows an artificial leg with a controllable motion damper, with the artificial leg in the stretched position.
Figure 2:
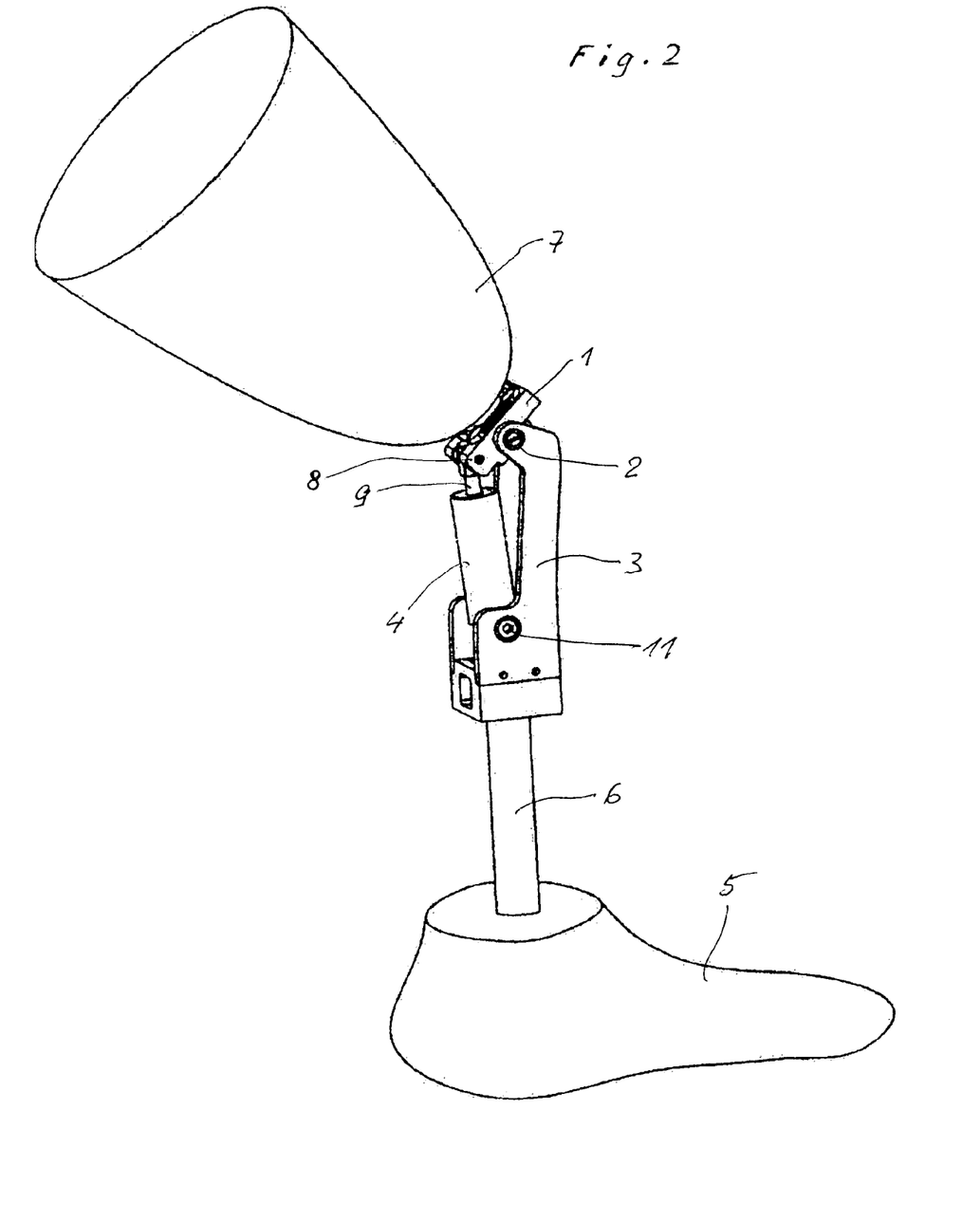
FIG. 2 shows the same artificial leg, with that portion of the artificial leg replacing the knee in the bent position.

The artificial leg schematically presented in FIGS. 1 and 2 is an artificial leg with the artificial knee joint 1, said knee joint 1 being rotatable about the shaft 2, said shaft 2 penetrating the upper lower leg part 3, wherein disposed on said upper lower leg part 3 in the direction towards the foot part 5 is the lower lower leg part 6, which acts as the connection between the upper lower leg part 3 and the foot part 5. Attached to the knee joint 1 in the direction away from the lower leg part 3 is the thigh part 7, which serves also to receive a thigh stump. When the knee joint 1 bends, its lever arm 8 is moved towards the foot part 5 (see FIG. 2), this correspondingly displacing the damping piston ram 9 of a motion damper presented in FIGS. 3 and 4. Said motion damper, identified by reference character 4 in FIGS. 1 and 2, damps the knee joint movements in accordance with a desired program, the motion damper 4 being slightly displaced in its position in relation to the upper lower leg part 3. In order to make such displacement possible, the motion damper 4 is supported, on its side facing the foot part 5, on the shaft 11. The control of the motion damper 4 by means of a program does not fall within the scope of the present invention. Reference may be made in this respect, for example, to the aforementioned GB 2328160.

Starting from the stretched position of the artificial leg as presented in FIG. 1, therefore, the artificial knee joint 1 can be rotated about the shaft 2 and, with the knee joint 1 approximately in the half-bent position, assumes the position presented in FIG. 2, in which the damping piston 10' (see FIGS. 3 and 4) is inserted further into the motion damper 4 in comparison with its position as presented in FIG. 1.

Inasmuch, this is basically a known design of the kind presented also in EP 0 857 838.

Figure 3:
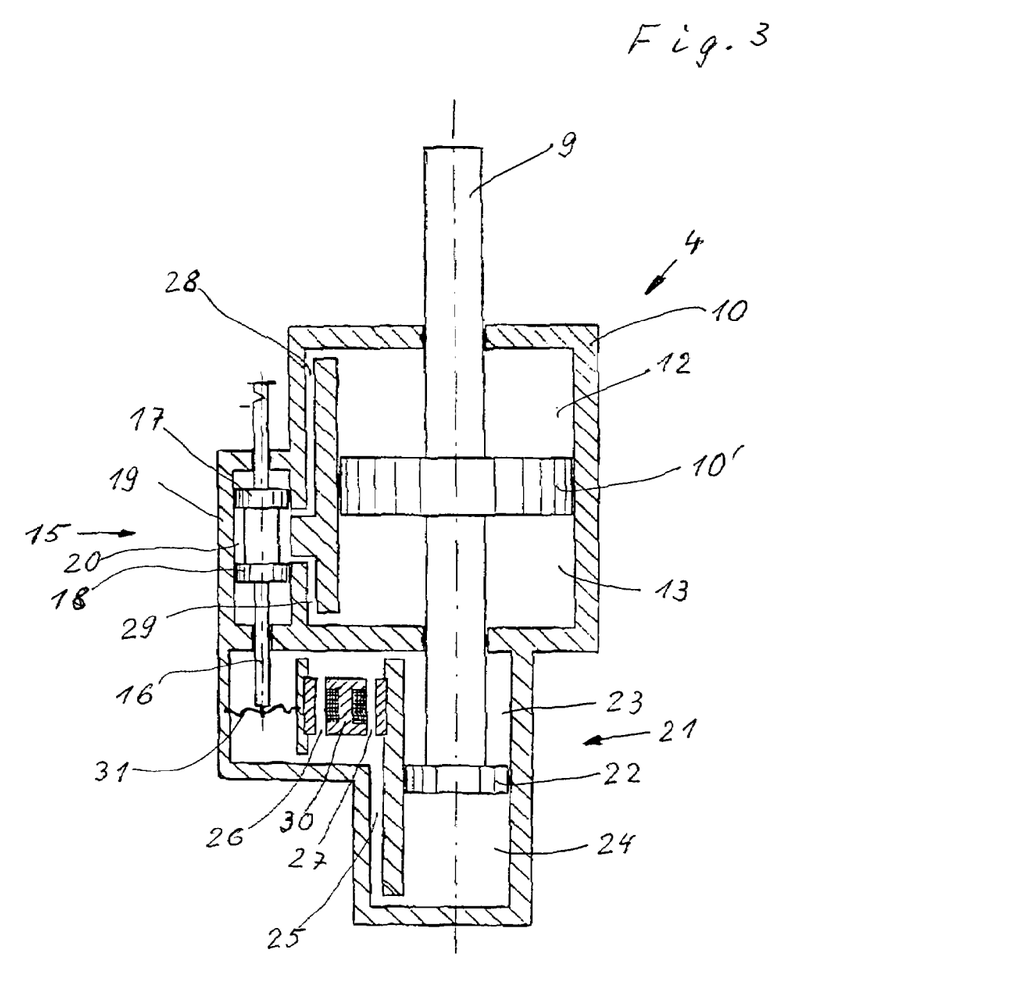
FIG. 3 shows a design of the motion damper in which the damping valve is disposed next to the damping cylinder.

FIG. 3 shows the internal construction of the motion damper 4 schematically presented in FIGS. 1 and 2. Said motion damper 4 comprises the damping piston ram 9, said damping piston ram 9 being displaceable in the damping cylinder 10 and co-displacing the damping piston 10'. The damping piston 10' divides the damping cylinder 10 into the two damping chambers 12 and 13, which damping chambers 12 and 13 are filled with a damping fluid, more particularly with a conventional damping oil. However, said damping fluid may also be a gas, such as air. The damping fluid is displaced when the damping piston 10' is moved, this giving rise to a corresponding flow in the connecting channel, said connecting channel consisting of the upper channel part 28 and the lower channel part 29. Both channel parts 28 and 29 are interconnected by the damping valve 15, wherein, when in its position as presented in FIG. 3, said damping valve 15 interconnects the two channel parts 28 and 29 in such a manner that, when the damping piston 10' is displaced, the damping valve 15 allows a pressure equalization between the damping chambers 12 and 13, said pressure equalization being virtually devoid of flow resistance.

The damping valve 15 contains the ram 16, which ram 16 acts as an actuator for the damping valve 15, wherein said ram 16, when displaced, displaces the two valve disks 17 and 18, which are displaceably supported in the damping valve cylinder 19. With the ram 16 in the position presented in FIG. 3, the space 20 between the two valve disks 17 and 18 forms a flow connection for the two channel parts 28 and 29, with the result that, with the damping valve 15 in the position shown in FIG. 3, the motion damper allows a movement of the damping piston 10' to remain virtually undamped.

When, however, the ram 16 displaces the two valve disks 17 and 18, with the result that said valve disks 17 and 18 more or less close the channel parts 28 and 29, said channel parts 28 and 29 terminating in the space 20, then, owing to the thereby caused increased flow resistance in the bypass channel formed by the channel parts 28 and 29, there is produced a resistance against the displacement of the damping piston 10' and thus a desired damping of the movement of the knee joint 1 (see FIGS. 1 and 2). This adjustment of the damping valve 15, which has a damping effect, will be more fully explained in the following.

The damping piston ram 9 projects into the slide piston unit 21 and displaces therein the slide piston 22, which slide piston 22 divides the slide piston unit 21 into two separate actuating chambers 23 and 24, said actuating chambers 23 and 24 being interconnected by the bypass channel 25. The slide piston unit 21 and the chambers connected to the actuating chambers 23 and 24 are filled with a magnetorheological fluid. When the damping piston 10' and thus the slide piston 22 are displaced, therefore, the magnetorheological fluid contained in the bypass channel 25 is caused to flow through the two parts 26 and 27 of the bypass channel 25. Arranged hydraulically in parallel with the bypass channel parts 26 and 27 is the elastic partition wall 31, which is formed by a diaphragm spring and which, owing to its elasticity, acts as a restoring spring for the thereto connected ram 16. This construction results, when the damping piston 10' is moved, in the following operating principle: the damping piston 10' acts on the slide piston 22, which exerts a positive and a negative pressure, respectively, on the actuating chambers 23 and 24, the respective pressure difference being equalized through the bypass channel 25. Initially, there is no pressure difference on the two sides of the partition wall 31, with the result, therefore, that the position of the ram 16 remains uninfluenced. When, however, the flow resistance for the magnetorheological fluid is increased in the two bypass channel parts 26 and 27, this gives rise to corresponding positive and negative pressures on the two sides of the partition wall 31, which partition wall 31 is thereupon correspondingly deflected and co-displaces the ram 16. The ram 16 displaces the valve disks 17 and 18, as a consequence of which the outlet of either channel part 28 or channel part 29 is constricted, this constricting the connecting channel for the two damping chambers 12 and 13. This results in corresponding damping of the movement of the damping piston 10' and therefore in the damping of the movement of the artificial leg presented in FIGS. 1 and 2.

The viscosity of the magnetorheological fluid flowing through the two bypass channel parts 26 and 27 is influenced by the magnetic field generator 30, said magnetic field generator 30 being a coil through which an electric current flows, said coil generating a magnetic field which is dependent on the respective strength of the current, said magnetic field being closed in known manner via the bypass channel parts 26 and 27. When the magnetic field becomes stronger in this region, the viscosity of the magnetorheological fluid is increased, this resulting in corresponding pressure differences on both sides of the partition wall 31 and therefore in a corresponding movement of the damping valve 15, this then finding expression in a corresponding damping of the motion damper 9/10.

It becomes evident from the above explanatory remarks that the motion damper, consisting of the damping piston 10' and the damping cylinder 10, acts via the damping valve 15 using a conventional damping fluid, wherein, however, advantageous use is made of the particular advantages of control, based on the electric signals of a program, of the damping of said motion damper by a damping valve controlled by a magnetorheological fluid, the energy for the operation of the damping valve being diverted from the movement of the damping piston via the slide piston unit, which slide piston unit, because it is filled with the magnetorheological fluid, allows the advantageous control of the damping valve by means of electric signals.

In the design of the motion damper presented in FIG. 3, the damping valve 15 is disposed laterally next to the damping cylinder 10. Conversely, in the illustrative embodiment presented in FIG. 4, the damping valve is arranged coaxially with the damping piston, wherein, compared with the illustrative embodiment in FIG. 3, this design offers a size advantage with regard to its accommodation in a motion damper, as shown in FIGS. 1 and 2.

Figure 4:
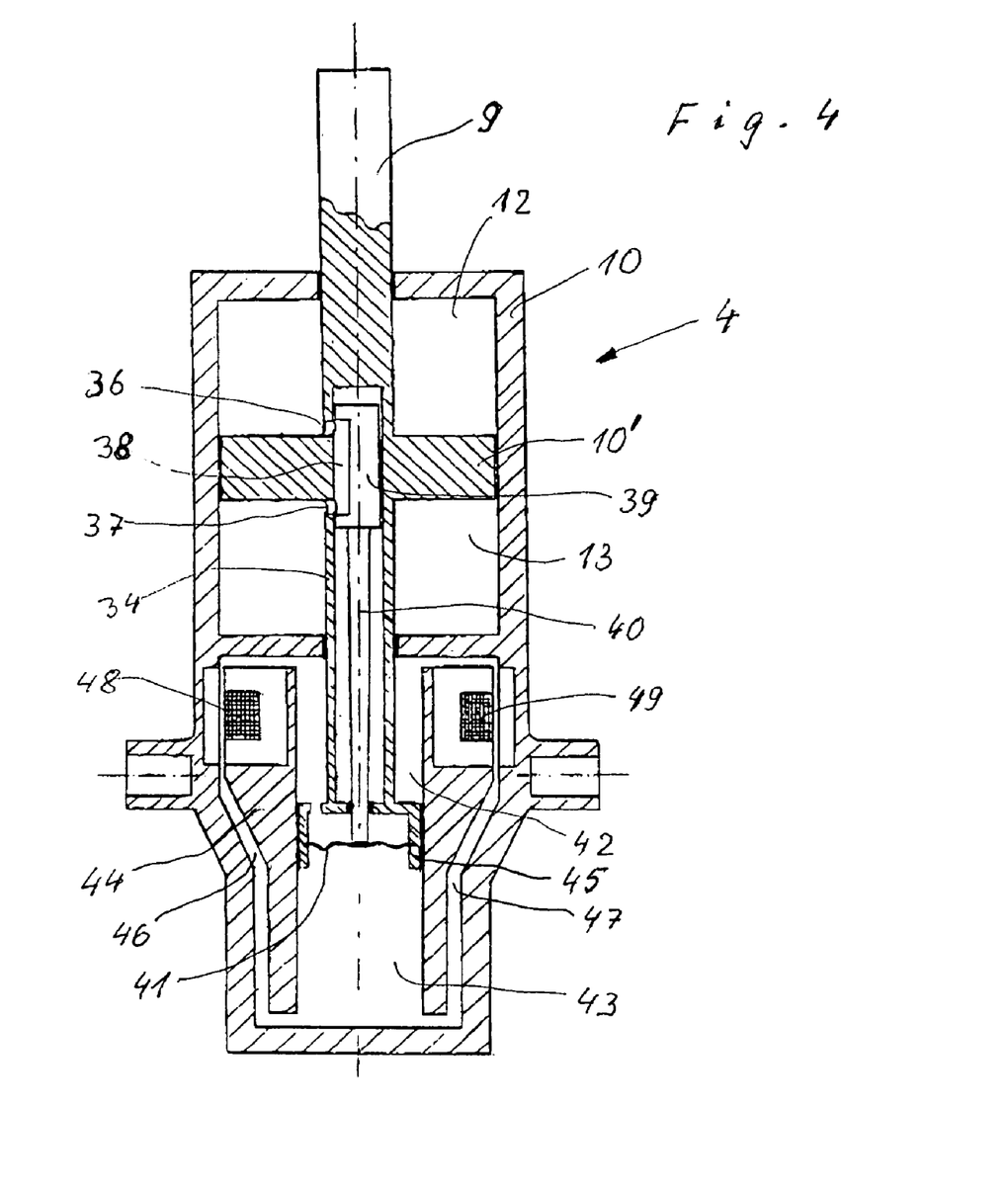
FIG. 4 shows a design of the motion damper in which the damping valve is coaxial with the damping piston.

Such a coaxial position is presented in FIG. 4. In the illustrative embodiment shown in FIG. 4, the motion damper, as in the illustrative embodiment shown in FIG. 3, comprises the damping piston ram 9 and the damping cylinder 10, in which damping cylinder 10 the damping piston ram 9 displaces the damping piston 10'. In this case, the damping piston ram 9 contains, in its extension, the pipe piece 34, the interior of which forms the bypass channel for the two damping chambers 12 and 13. Said bypass channel extends over the two openings 36 and 37 in the pipe piece 34, said openings 36 and 37 leading inwardly into the hollow space 38. Displaceably held in the pipe piece 34 is the valve part 39, which valve part 39 encompasses the hollow space 38 and, in the position presented in FIG. 4, interconnects the damping chambers 12 and 13 via the openings 36 and 37. When the valve part 39 is displaced, the openings 36 and 37 are more or less blocked off, this corresponding to the displacement of the valve disks 17 and 18 in FIG. 3.

The displacement of the valve part 39 is accomplished via the ram 40, which, similarly to the illustrative embodiment in FIG. 3, is moved by the partition wall 41, said partition wall 41 being in the form of a diaphragm spring. The partition wall 41 forms an elastic restoring spring for the ram 40 between two chambers 42 and 43 of a slide piston unit formed by the cylinder 44 and the therein axially movable slide piston 45. The slide piston 45 is suspended from the pipe piece 34, said pipe piece 34 being an extension of the damping piston ram 9, and is moved in reciprocating manner when the damping piston ram 9, i.e. the knee joint, is moved. As long as the ram 40 is not prevented from being co-displaced by the damping piston ram 9, there is no displacement of the valve part 39 in relation to the openings 37 and 38, with the result that, with simultaneous movement of the damping piston 10', the damping fluid contained in the two damping chambers 12 and 13 is able to flow freely via the hollow space 38, it therefore being impossible for a pressure difference—which would produce a damping effect—to be created in the two damping chambers 12 and 13. The movement of the damping piston ram 9 and therefore of the artificial knee joint thus remains undamped.

This movement of the ram 40 is also accompanied by a corresponding displacement of the partition wall 41, which partition wall 41 displaces the magnetorheological fluid contained in the chambers 42 and 43, this taking place without hindrance via the bypass channel parts 46 and 47, said bypass channel parts 46 and 47 interconnecting the two chambers 42 and 43. Similarly to the illustrative embodiment in FIG. 3, said bypass channel parts 46 and 47 are provided with magnetic field generators 48 and 49, wherein, given a corresponding flow of current and thus a magnetic field acting on the bypass channel parts 46 and 47, said magnetic field generators 48 and 49 correspondingly influence the viscosity of the magnetorheological fluid and thereby correspondingly hinder the displacement of the partition wall 41. The magnetic field generators 48 and 49 may be in the form of ring pole magnets. This results in a relative movement between the—as it were—fixed ram 40 and the slide piston 45, this finding expression in a corresponding relative movement between the valve part 39 and the openings 36 and 37. This gives rise to an adjustment of the damping valve containing the valve part 39, as a result of which the movement of the ram 9, and therefore of the artificial leg, is correspondingly damped. With regard to operating principle, therefore, the illustrative embodiment in FIG. 4 is identical with that in FIG. 3, with the consequence that reference is made in this respect to the explanatory remarks presented in relation to FIG. 3.

The advantage of the design of the illustrative embodiment shown in FIG. 4 consists in the fact that, in this design of motion damper, the damping valve and the associated control device are arranged coaxially one behind the other, this simplifying the placement of such an embodiment of a motion damper, as presented in FIGS. 1 and 2.

The construction of the motion damper with damping cylinder and axially therewith moved damping piston, as presented in FIGS. 3 and 4, can also be accomplished using rotary pistons which move in rotating manner in a damping cylinder. This is presented in the illustrative embodiment shown in FIG. 5a to e, FIG. 5a showing a section along line A-A from FIG. 5b and FIG. 5c showing a section along line B-B from FIG. 5b.

Figures 5A, 5A, 5A, 5A, 5B, 5C, 5E:
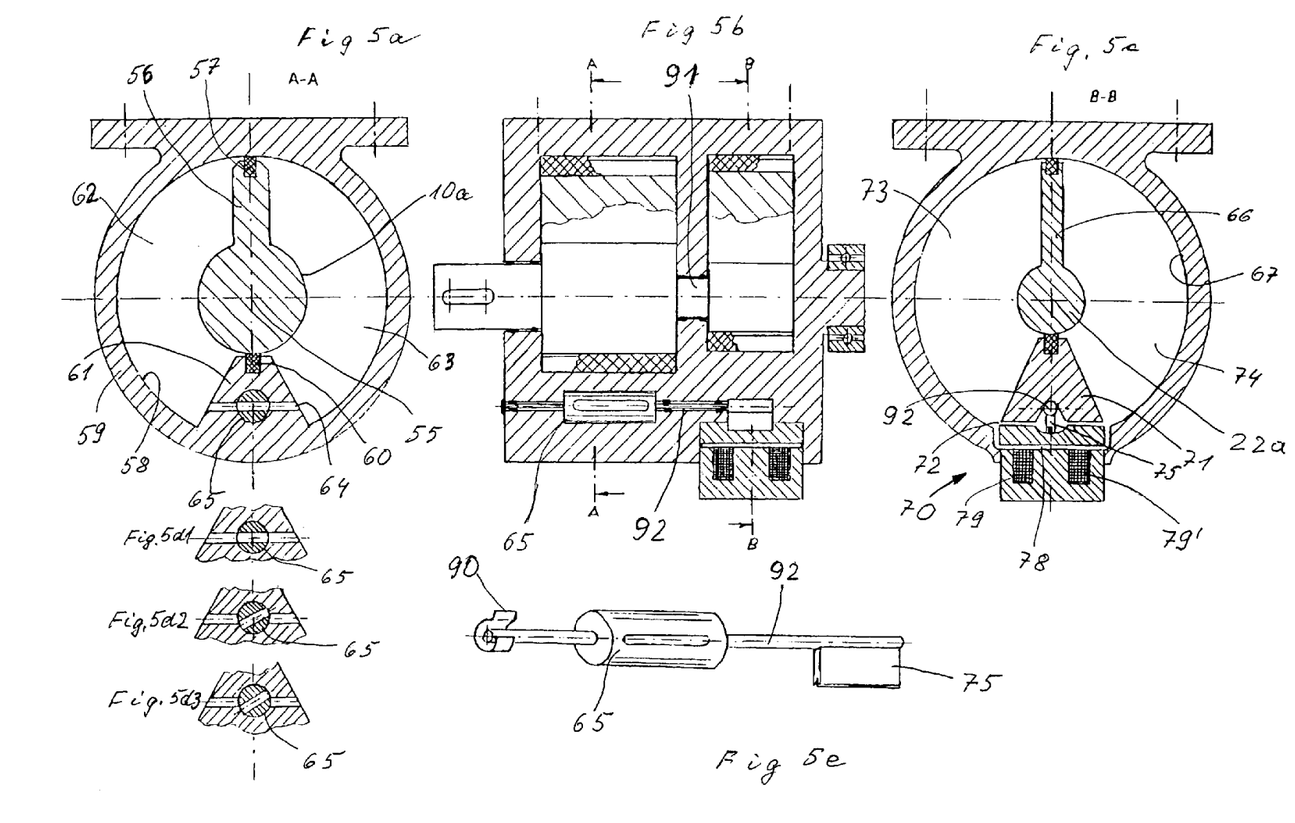

In the illustrative embodiment presented in FIG. 5a, the damping piston is in the form of a rotary piston 10a which rotates about the axis 55. The rotary piston 10a comprises the vane 56, which is sealingly supported via the seal 57 on the inside wall 58 of the damping cylinder 59. On its side facing away from the damping vane 56, the rotary piston 10a maintains sealing contact with the seal 60, which seal 60 is embedded in the sectorially extending wall 58 of the damping cylinder 59. Thus formed in the damping cylinder 59 are the two damping chambers 62 and 63, which damping chambers 62 and 63 are separated from each other by the rotary piston 10a with the damping vane 56.

The two damping chambers 62 and 63 are interconnected by the connecting channel 64, in which connecting channel 64 is rotatably installed the damping valve 65, the mode of operation of which will be described in fuller detail in connection with FIGS. 5d1, 5d2 and 5d3. With the damping valve 65 in the position presented in FIG. 5a, the damping fluid contained in the two damping chambers 62 and 63 is able to flow virtually without hindrance from one damping chamber 62 into the other damping chamber 63 and vice versa.

Connected coaxially to the rotary piston 10a is the slide piston unit 70 with the slide piston 22a (see FIG. 5c), wherein said slide piston 22a, like the rotary piston 10a in FIG. 5a, is also in the form of a rotary piston and is co-rotated when the rotary piston 10a rotates. Like the rotary piston 10a in FIG. 5a, the slide piston 22a comprises the vane 66, which vane 66 is co-rotated when the slide piston 22a rotates. The sealing of the slide piston 22a and of the vane 66 with respect to the inside wall 67 of the slide piston unit shown in FIG. 5c is accomplished in the same manner as described above in connection with the rotary piston 10a.

When an artificial leg is bent, the motion damper presented in FIG. 5a to 5e is operated in a manner which corresponds to the operation of the motion dampers shown in FIGS. 3 and 4, i.e. the rotary piston 10a is rotated when the artificial knee joint is bent, as a result of which the slide piston 22a with its vane 66 is also rotated as in FIG. 5c, since the rotary piston 10a and the slide piston 22a are interconnected in rotationally fixed manner by means of the connecting piece 91 shown in FIG. 5b.

Similarly to the design shown in FIG. 5a, the wall 71 projects into the interior of the slide piston cylinder 70, said wall 71 containing a connection 72 between the two actuating chambers 73 and 74. Fitted into said connection 72 is a rotary vane 75, which rotary vane 75 is correspondingly rotated by a pressure acting on one of its sides. The slide piston unit 70, containing the slide piston 22a, is filled with magnetorheological fluid, which, when the vane 66 rotates, is displaced from one actuating chamber 73 into the other actuating chamber 74 via the connection 72 and correspondingly co-displaces the rotary vane 75. Said co-displacement is opposed by the rotary vane 75 with a resistance from a correspondingly adjusted torsion spring (90), similarly to the case with the partition wall 31 presented in FIG. 3. Hydraulically, the connection 72 is connected in parallel with the bypass channel 78, wherein said bypass channel 78, when there is transmissivity, allows the magnetorheological fluid to flow virtually without hindrance from one actuating chamber 73 into the other actuating chamber 74 and vice versa. Installed in said bypass channel 78 are the two magnetic field generators 79 and 79', which, through a correspondingly adjusted flow of current, generate a magnetic field which controls the flow of fluid through the bypass channel 78. The magnetic field generators 79 and 79' may be in the form of ring pole magnets. The more the flow of the magnetorheological fluid through the bypass channel 78 is hindered by the magnetic field generators 79 and 79', the greater is the effect of the pressure difference in the two actuating chambers 73 and 74, this finding expression in a corresponding movement of the rotary vane 75. The shaft 92 of the rotary vane 75 is, as shown in FIG. 5e, directly connected to the damping valve 65, wherein said damping valve 65, when it rotates, as clearly shown in FIGS. 5d1, 5d2 and 5d3, more or less hinders the flow of damping fluid through the connecting channel 64, thereby causing a corresponding damping of the rotational movement of the vane 56 and therefore of the damping piston 10a.

FIG. 5e illustrates the connection between the rotary vane 75 and the damping valve 65 through the common shaft 92.

Figure 6:
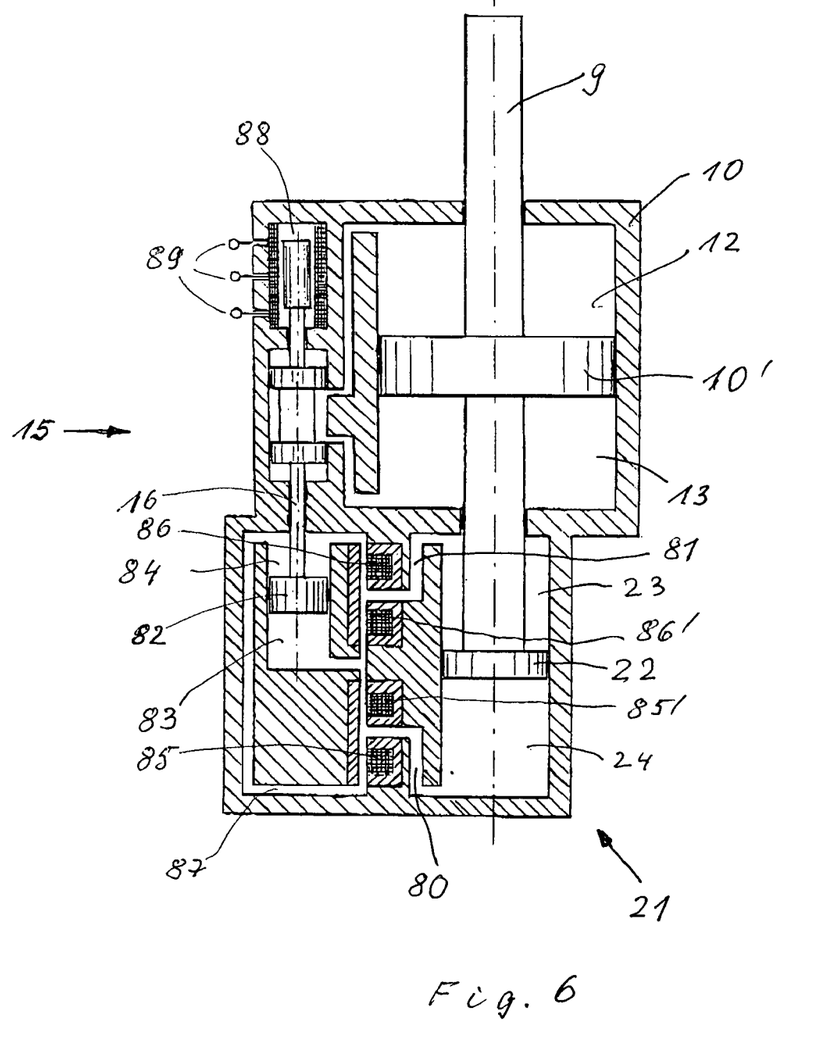
FIG. 6 shows a design of the motion damper in which the damping valve is adjustable to any desired positions.

With the above-presented illustrative embodiments of a controllable motion damper, the movement of the damping piston with each stroke in either direction is damped by the magnetorheological fluid, depending on the strength of the existing magnetic field. At the end of a stroke, therefore, the damping effect also ends. However, it is also possible to adjust the damping effect permanently to a fixed value which is adjusted through excitation of the respective magnetic field generator. An illustrative embodiment thereof is presented in FIG. 6, which, with regard to the damping piston with damping cylinder and damping valve, is identical with the design shown in FIG. 3. However, in the illustrative embodiment shown in FIG. 6, the movement of the damping valve 15 (same reference character as in FIG. 3) is accomplished in the following manner:

The damping valve 15 is adjusted via the ram 16 and, as was described in connection with the illustrative embodiment according to FIG. 3, thereby changes its position and the damping of the damping piston ram 9. As in the case of the illustrative embodiment according to FIG. 3, the energy for the displacement of the ram 16 is diverted from the movement of the damping piston ram 9, which, when it and the slide piston 22 are moved, displaces a magnetorheological fluid in the channels 80 and 81, said magnetorheological fluid filling the region with the slide piston unit 21, as shown in the illustrative embodiment according to FIG. 3. The channels 80 and 81 extend into the chambers 83 and 84 separated by the control piston 82, i.e. a pressure in chamber 83 or 84 causes a corresponding axial displacement of the control piston 82. Said pressure on the respective chamber 83 or 84 is controlled via the magnetic field generators 85 and 85' as well as 86 and 86', which each act on the connection from channel 80 or 81 to chamber 83 or 84 and thus correspondingly influence the displacement of the control piston 82, depending on the strength of their magnetic field. The channel 80 is connected to the chamber 84 via the connection 87. It is therefore possible to act on the respectively desired side of the control piston 82 through each of the two channels 80 and 81, as a consequence of which the control piston 82 is selectively displaced according to the control of the magnetic field generators. With this displacement of the control piston 82, the damping valve. 15 is correspondingly adjusted via the ram 16, this resulting in a fixed damping of the damping piston 9.

This adjustment of the damping is indicated via the sensor 88, said sensor 88 being connected to the ram 16 and to the damping valve 15 and containing a magnetic sensor of known construction, wherein said magnetic sensor, depending on its adjustment, activates various devices which reproduce the adjustment of the damping valve 15 and communicate said adjustment to a controller.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. Controllable motion damper (4) with a damping piston (10'), said damping piston (10') separating two damping chambers (12, 13) from each other in a damping cylinder (10), and with a damping valve (15) disposed in a connecting channel (28, 29) of the two damping chambers (12, 13), the transmissivity of said damping valve (15) for a damping fluid contained in the motion damper (4) being controlled by a control device (21, 16), characterized in that both damping chambers (12, 13) are filled with an electromagnetically uninfluenceable damping fluid, the control device having a slide piston unit (21) filled with a magnetorheological fluid, said slide piston unit (21) having a slide piston (22) operatively coupled to the damping piston (10'), wherein, through the intermediary of the magnetorheological fluid, said magnetorheological fluid being influenceable by controllable magnetic field generators (30) with regard to its flow resistance, said slide piston (22) acts on an actuator (16) connected to the damping valve (15) for controlling the movement of the damping piston (10').

2. Motion damper according to claim 1, characterized in that the slide piston unit (21) contains two actuating chambers (23, 24) separated by the slide piston (22), with a bypass channel (26, 27) interconnecting said actuating chambers (23, 24), the flow resistance of said bypass channel (26, 27) being adjustable by the magnetic field generators (30).

3. Motion damper according to claim 2, characterized in that the damping valve (15) is connected to a ram (16) forming the actuator and guided by a restoring spring, said ram (16) being adjustably connected to a partition wall (31), said partition wall (31) dividing the slide piston unit (21) into the two actuating chambers (23, 24) interconnected by the bypass channel (26, 27).

4. Motion damper according to any one of claims 1 to 3, characterized in that the damping valve (15) is disposed next to the damping cylinder (10) and the slide piston unit (21) is coaxial with the damping cylinder (10).

5. Motion damper according to any one of claims 1 to 3, characterized in that the damping valve (38, 39) is coaxial with the damping piston (10') and is a constituent part of the damping piston (10').

6. Motion damper according to claim 1 or 2, characterized in that the motion damper and the slide piston unit are each in the form of a rotary piston (10a, 22a) and the damping valve (65) and the bypass channel (72, 78) are each provided in a sectorially extending wall (61, 71), the damping valve being in the form of a rotary valve (65) and the bypass channel (72) containing a rotary vane (75) as a constituent part of the actuator, wherein rotary valve (65) and rotary vane (75) are interconnected by a shaft (92) and are held in the normal position by a torsion spring (90).

7. Motion damper according to claim 1 or 2, characterized in that the damping valve (15) is connected to the actuator (16) by a control piston (82), said actuator (16) being connected to the slide piston unit (21) by a plurality of bypass channels (80, 81) each adjustable by a magnetic field generator (85, 86), wherein, depending on the activation of the individual magnetic field generators (85, 86), said bypass channels (80, 81) adjust the control piston (82) to any desired positions and more especially to positions which follow the movement of the slide piston (22).

8. Controllable motion damper (4) with a damping piston (10'), said damping piston (10') separating two damping chambers (12, 13) from each other in a damping cylinder (10), and with a damping valve (15) disposed in a connecting channel (28, 29) of the two damping chambers (12, 13), the transmissivity of said damping valve (15) for a damping fluid contained in the motion damper (4) being controlled by a control device (21, 16), characterized in that both damping chambers (12, 13) are filled with an electromagnetically uninfluenceable damping fluid, the control device having a slide piston unit (21) filled with an electrorheological fluid, said slide piston unit (21) having a slide piston (22) operatively coupled to the damping piston (10'), wherein, through the intermediary of the electrorheological fluid, said electrorheological fluid being influenceable by a controllable electric field with regard to its flow resistance, said slide piston (22) acts on an actuator (16) connected to the damping valve (15) for controlling the movement of the damping piston (10').

9. Motion damper according to claim 8, characterized in that the slide piston unit (21) contains two actuating chambers (23, 24) separated by the slide piston (22), with a bypass channel (26, 27) interconnecting said actuating chambers (23, 24), the flow resistance of said bypass channel (26, 27) being adjustable by the electric field.

10. Motion damper according to claim 9, characterized in that the damping valve (15) is connected to a ram (16) forming the actuator and guided by a restoring spring, said ram (16) being adjustably connected to a partition wall (31), said partition wall (31) dividing the slide piston unit (21) into the two actuating chambers (23, 24) interconnected by the bypass channel (26, 27).

* * * * *